United States Patent [19]

Woessner et al.

[11] 4,115,453

[45] Sep. 19, 1978

[54] BICYCLOALKYL DERIVATIVES OF PROSTAGLANDINS $PGE_1$ ALCOHOLS

[75] Inventors: Warren Dexter Woessner; Charles John Sih; Harold Clinton Kluender; Henry Clifford Arndt; William Gerard Biddlecom, all of Madison, Wis.

[73] Assignee: Miles Laboratories, Inc., Elkhart, Ind.

[21] Appl. No.: 818,057

[22] Filed: Jul. 22, 1977

Related U.S. Application Data

[62] Division of Ser. No. 657,221, Feb. 11, 1976, Pat. No. 4,074,063.

[51] Int. Cl.$^2$ ............................................. C07C 49/46
[52] U.S. Cl. ................................................. 260/586 G
[58] Field of Search ..................... 260/617 HF, 586 G

[56] References Cited

U.S. PATENT DOCUMENTS 3,880,883 4/1975 Caton et al. ...................... 260/514 D

FOREIGN PATENT DOCUMENTS 151,843 12/1975 Japan ........................................ 260/468
1,456,838 11/1976 United Kingdom ..................... 260/514

Primary Examiner—Gerald A. Schwartz
Attorney, Agent, or Firm—Richard W. Winchell

[57] ABSTRACT

Novel bicycloalkyl analogues or derivatives of prostaglandin A, E and F are useful modifiers of smooth muscle activity. The compounds have valuable pharmacological properties as platelet antiaggregating agents and gastric antisecretory agents. The compounds are also valuable pharmacological agents for increasing femoral blood flow and decreasing blood pressure and heart rate.

5 Claims, No Drawings

BICYCLOALKYL DERIVATIVES OF PROSTAGLANDINS PGE₁ ALCOHOLS

This is a division of application Ser. No. 657,221, filed Feb. 11, 1976 now U.S. Pat. No. 4,074,063.

BACKGROUND OF THE INVENTION

1. Field of the Invention

Compounds of this invention are analogues of natural prostaglandins.

Natural prostaglandins are twenty-carbon atom alicyclic compounds related to prostanoic acid which has the following structure:

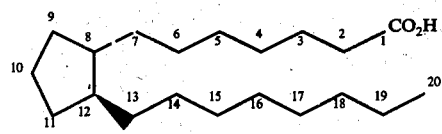

(I).

By convention, the carbon atoms of I are numbered sequentially from the carboxylic carbon atom. An important stereo-chemical feature of I is the trans-orientation of the side-chains $C_1$–$C_7$ and $C_{13}$–$C_{20}$. All natural prostaglandins have this orientation. In I, as elsewhere in this specification, a dashed line (---) indicates projection of a covalent bond below the plane of a reference carbon atom (alpha-configuration), while a wedged line (◄) represents direction above that plane (beta-configuration). Those conventions apply to all compounds subsequently discussed in this specification.

In one system of nomenclature suggested by N. A. Nelson (J. Med. Chem., 17: 911 (1972), prostaglandins are named as derivatives or modifications of the natural prostaglandins. In a second system, the I.U.P.A.C. (International Union of Pure and Applied Chemistry) system of nomenclature, prostaglandins are named as substituted heptanoic acids. Yet a third system of nomenclature is frequently used by those skilled in the prostaglandin art. In this third system (also described by Nelson), all prostaglandins are named as derivatives or modifications of prostanoic acid (structure I) or prestane (the hydrocarbon equivalent of structure I). This system is used by Chemical Abstracts and may become an I.U.P.A.C. accepted system.

Natural prostaglandins have the structures,

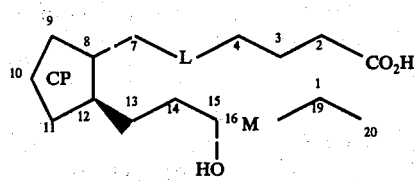

(II)

in which:

L and M may be ethylene or cis-vinylene radicals and the five membered ring

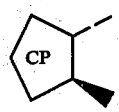

may be:

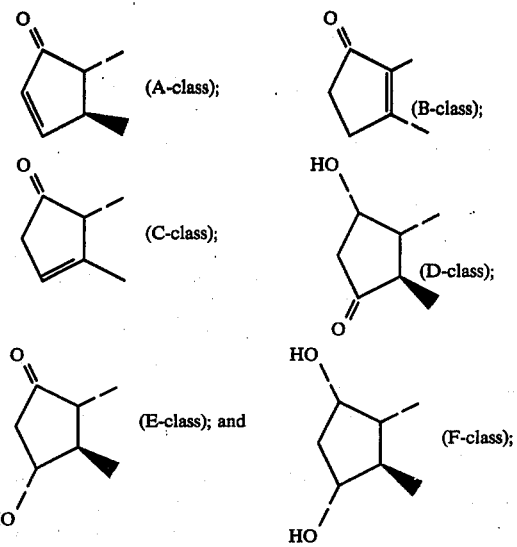

Prostaglandins are classified according to the functional groups present in the five-membered ring and the presence of double bonds in the ring or chains. Prostaglandins of the A-class (PGA or prostaglandin A) are characterized by an oxo group at $C_9$ and a double bond at $C_{10}$–$C_{11}$ ($\Delta^{10,11}$); those of the B-class (PGB) have an oxo group at $C_9$ and a double bond at $C_8$–$C_{12}$ ($\Delta^{8,12}$); compounds of the C-class (PGC) contain an oxo group at $C_9$ and a double bond at $C_{11}$–$C_{12}$ ($\Delta^{11,12}$); members of the D-class (PGD) have an oxo group at $C_{11}$ and an alpha-oriented hydroxy group at $C_9$; prostaglandins of the E-class (PGE) have an oxo group at $C_9$ and an alpha-oriented hydroxyl group at $C_{11}$; and members of the F-class (PGF) have an alpha-directed hydroxyl group at $C_9$ and an alpha-oriented hydroxyl group at $C_{11}$. Within each of the A, B, C, D, E, and F classes of prostaglandins are three subclassifications based upon the presence of double bonds in the side-chains at $C_5$–$C_6$, $C_{13}$–$C_{14}$, or $C_{17}$–$C_{18}$. The presence of a trans-unsaturated bond only at $C_{13}$–$C_{14}$ is indicated by the subscript numeral 1; thus, for example, PGE₁ (or prostaglandin E₁) denotes a prostaglandin of the E-type (oxo group at $C_9$ and an alpha-hydroxyl at $C_{11}$) with a trans-double bond at $C_{13}$–$C_{14}$. The presence of both a trans-double bond at $C_{13}$–$C_{14}$ and a cis-double bond at $C_5$–$C_6$ is denoted by the subscript numeral 2; for example, PGE₂. Lastly, a trans-double bond at $C_{13}$–$C_{14}$, a cis-double bond at $C_5$–$C_6$ and a cis-double bond at $C_{17}$–$C_{18}$ is indicated by the subscript numeral 3; for example, PGE₃. The above notations apply to prostaglandins of the A, B, C, D, and F series as well, however, in the latter the alpha-orientation of the hydroxyl group at $C_9$ is indicated by the subscript Greek letter α after the numerical subscript.

The three systems of nomenclature as they apply to natural PGF₃α are shown below:

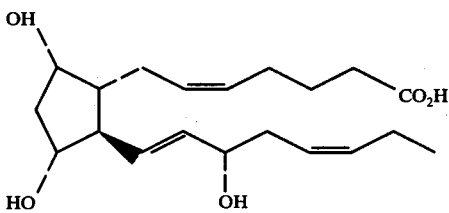

Nelson System:

Prostaglandin F$_{3\alpha}$ or PGF$_{3\alpha}$ (shorted form) I.U.P-.A.C. System:

7-[3R, 5S-Dihydroxy-2R-(3S-hydroxy-1E,5Z-octadienyl)cyclopent-1R-yl]-5Z-heptenoic acid Third System (Chemical Abstracts):

(5Z, 9α, 11α, 13E, 15S, 17Z)-9,11,15-trihydroxyprosta-5,13,17-trien-1-oic acid.

It is important to note that in all natural prostaglandins there is an alpha-oriented hydroxyl group at C$_{15}$. In the Cahn-Ingold-Prelog system of defining stereochemistry, that C$_{15}$ hydroxyl group is in the S-configuration. The Cahn-Ingold-Prelog system is used to define stereochemistry of any asymmetric center outside of the carbocyclic ring in all three systems of nomenclature described above. This is in contrast to some prostaglandin literature in which the α,β designations are used, even at C$_{15}$.

11-Deoxy derivatives of PGE and PGF molecules do not occur as such in nature, but constitute a class of compounds which possess biological activity related to the parent compounds. Formula II represents 11-deoxy PGE and PGF compounds when:

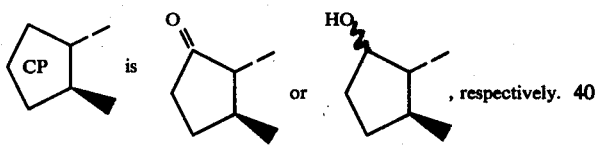

, respectively.

In this formula, and others of this patent specification a swung dash or serpentine line (∼) denotes a covalent bond which can be either in the alpha configuration (projecting below the plane of a reference carbon atom) or in the beta configuration (projecting above the plane of a reference carbon atom).

PGF$_\beta$ molecules also do not occur as such in nature, but constitute a class of compounds which possess biological activity related to the parent compounds. Formula II represents PGF$_\beta$ compounds when:

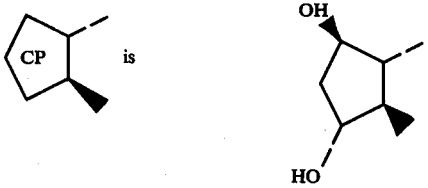

9-Deoxy derivatives of PGE do not occur as such in nature, but constitute a class of compounds which possess biological activity related to the parent compounds. Formula II represents 9-deoxy PGE compounds when:

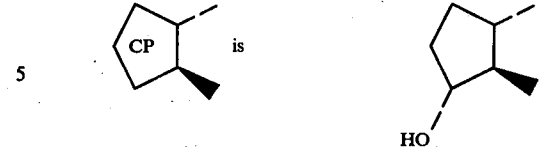

9-Deoxy-Δ$^{9,10}$ derivatives of PGE do not occur as such in nature, but constitute a class of compounds which possess biological activity related to the parent compounds. Formula II represent 9-deoxy-Δ$^{9,10}$ PGE compounds when:

9-Homo- and 9α-homo-11-deoxy-derivative of PGE and PGF molecules do not occur as such in nature, but constitute a class of compounds which possess biological activity related to the parent compounds. Formula II represents 9α-homo- and 9α-homo-11-deoxy-compounds of PGE and PGF when:

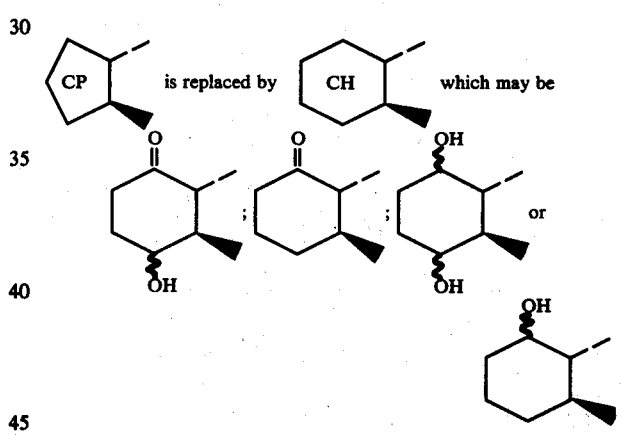

11-Homo-derivatives of PGE, PGF and PGA molecules do not occur as such in nature, but constitute classes of compounds which are expected to possess biological activity related to the parent compounds. Formula II represents 11α-homo-derivatives of PGE, PGF and PGA molecules when:

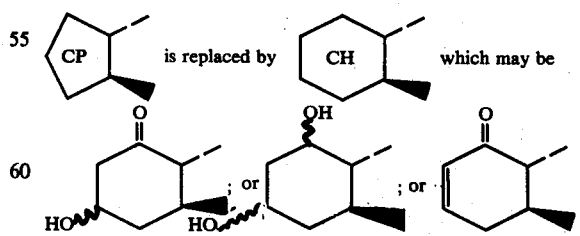

11-Epi-PGE and PGF molecules do not occur as such in nature, but constitute classes of compounds which possess biological activity related to the parent compounds. Formula II represents 11-epi-compounds of PGE and PGF when:

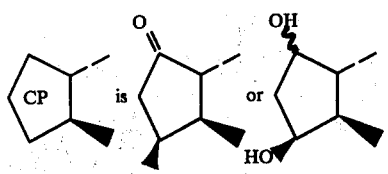

8Iso-, 12iso or 8,12-bis iso (ent) prostaglandins do not occur as such in nature, but constitute classes of compounds which possess biological activity related to the parent compounds. Formula II represents 8iso-, 12iso- or 8,12-bis iso (ent) compounds when:

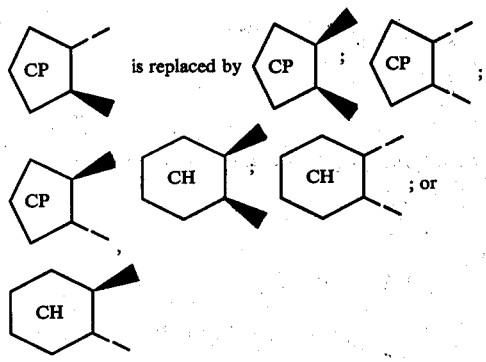

These iso modifications of Formula II may be divided into all of the sub-classes with varying ring oxygenation as described above.

Recent research indicates that prostaglandins are ubiquitous in animal and that prostaglandins, as well as their synthetic analogues, have important biochemical and physiological effects in mammalian endocrine, reproductive, central and peripheral nervous, sensory, gastro-intestinal, hematic, respiratory, cardiovascular, and renal systems.

In mammalian endocrine systems, experimental evidence indicates prostaglandins are involved in the control of hormone synthesis or release in hormone-secretory glands. In rats, for example, $PGE_1$ and $PGE_2$ increase release of growth hormone while $PGA_1$ increased synthesis of that hormone. In sheep, $PGE_1$ and $PGF_{1\alpha}$ inhibit ovarian progesterone secretion. In a variety of mammals, $PGF_{1\alpha}$ and $PGF_{2\alpha}$ act as luteolytic factors. In mice, $PGE_1$, $PGE_2$, $PGF_{1\alpha}$ and $PGF_{1\beta}$ increase thyroid activity. In hypophysectomized rats, $PGE_1$, $PGE_2$ and $PGF_{1\alpha}$ stimulate steroidogenesis in the adrenal glands.

In the mammalian male reproductive system, $PGE_1$ contracts the smooth muscle of the vas deferens. In the female reproductive system, PGE and $PGF_\alpha$ compounds contract uterine smooth muscle. In general, PGE, PGB and PGA compounds relax in vitro human uterine muscle strips, while those of the $PGF_\alpha$ class contract such isolated preparations. PGE compounds in general promote fertility in the female reproductive system while $PGF_{2\alpha}$ has contragestational effects. $PGF_{2\alpha}$ also appears to be involved in the mechanism of menstruation. In general, $PGE_2$ exerts potent oxytocic effects in inducing labor, while $PGF_{2\alpha}$ induces spontaneous abortions in early pregnancy.

$PGF_\alpha$ and PGE compounds have been isolated from a variety of nervous tissue and they seem to act as neurotransmitters. $PGE_1$ retards wheras $PGF_{2\alpha}$ facilitates transmission in motor pathways in the central nervous system. It has been reported that $PGE_1$ and $PGE_2$ inhibit transmitter release from adrenergic nerve endings in the guinea pig.

Prostaglandins stimulate contraction of gastrointestinal smooth muscle in vivo and in vitro. In dogs, $PGA_1$, $PGE_1$ and $PGE_2$ inhibit gastric secretion. $PGA_1$ exhibits similar activity in man.

In most mammalian respiratory tracts, compounds of the PGE and PGF class relax in vitro preparations of tracheal smooth muscle. In that preparation, $PGE_1$ and $PGE_2$ relax while $PGF_{2\alpha}$ contracts the smooth muscle. PGE and PGF compounds are normally found in the human lung, and it is postulated that some cases of bronchial asthma involve an imbalance in the production or metabolism of these compounds.

Prostaglandins are involved in certain hematic mechanisms in mammals. $PGE_1$, for example, inhibits thrombogenesis in vitro through its effects on blood platelets.

In a variety of mammalian cardiovascular systems, compounds of the PGE and PGA class are vasodilators whereas those of the $PGF_\alpha$ class are vasoconstrictors, by virtue of their action on vascular smooth muscle.

Prostaglandins are naturally found in the kidney and reverse experimental and clinical renoprival hypertension.

The clinical implications of prostaglandins and their analogues are far-ranging and include, but are not limited to the following: in obstetrics and gynecology, they may be useful in fertility control, treatment of menstrual disorders, induction of labor, and correction of hormone disorders; in gastroenterology, they may be useful in the treatment of peptic ulcers and various disorders involving motility, secretion, and absorption in the gastrointestinal tract; in the respiratory area, they may be beneficial in therapy of bronchial asthma and other diseases involving bronchoconstriction; in hematology, they may have utility as anti-clotting agents in diseases such as venous thrombosis, thrombotic coronary occlusion and other diseases involving thrombi; in circulatory diseases they have therapeutic utility in hypertension, peripheral vasopathies, and cardiac disorders.

For a more complete review of chemical, physiological and pharmacological aspects of the prostaglandin, consult the following references: The Prostaglandins, Vol. I., P. Ramwell, Ed., New York, Plenum Press, 1973; Ann. N.Y. Acad. Sci., 180: 1–568(1971): and Higgins and Braunwald, J. Am. Med. Assn., 53: 92–112(1972).

DESCRIPTION OF THE PRIOR ART

Great Britain Patent Application No. 027,844 filed June 14, 1971 discloses cycloalkyl or adamantyl derivatives of prostaglandins.

Netherland Pat. No. 7,315,307 discloses cycloalkyl, adamantyl or 2-norbornyl derivatives of prostaglandins.

SUMMARY

Novel and useful bicycloalkyl analogues of prostaglandins having the following structural Formula III constitute the subject matter of this invention:

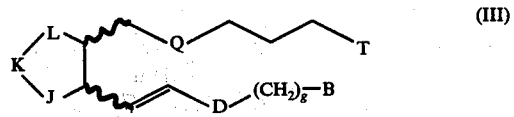

In Formula III:

g is an integer having a value of from 0 to 10;

D is a R-hydroxymethylene or S-hydroxymethylene radical;

J is a methylene, R-hydroxymethylene, S-hydroxymethylene or a methine radical such that J is methine only when K is methine;

K is a methylene, ethylene or a methine radical such that K is ethylene only when J is methylene and K is methine only when J is methine to form a carbon-carbon double covalent bond between J and K;

L is a carbonyl, R-hydroxymethylene or S-hydroxymethylene radical;

Q is an ethylene or Z-vinylene radical;

T is an alkoxycarbonyl having from 1 to 3 carbon atoms inclusive in the alkyl chain, carboxyl, or hydroxymethyl radical or pharmacologically acceptable nontoxic carboxy salts; and B is a bicycloalkyl radical of the formula

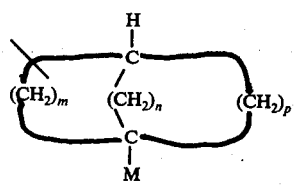

where m and p are integers having a value of from 1 to 4; n is an integer having a value of from 0 to 4 such that n is not 1 when m and p are both 2; and the sum of m, n and p is greater than or equal to 3 and where the point of attachment of the alkyl chain $(CH_2)_g$ to the bicycloalkyl radical is in the $(CH_2)_m$ bridge or bridgehead position.

The numbering system and the stereochemistry nomenclature used for the prostaglandins of this invention are according to the I.U.P.A.C. definitive and tentative rules which designate the carboxylic acid side chain as the parent compound. In Formula III, a swung dash or serpentive line (∼) denotes a covalent bond which can be either in the alpha configuration (projecting below the plane of a reference carbon atom) or in the beta configuration (projecting above the plane of a reference carbon atom). As used herein, cis or trans isomerism around double bonds respectively is designated by affixes Z (zusammen) and E (entgegen). Chirality around asymmetric carbon atoms is designated by affixes R (rectus) and S (sinister).

Analogues or derivatives of the A-, E-, and F- classes of the natural prostaglandins are represented by Formula III. Thus when, L is carbonyl, and both J and K are methine radicals, III represents analoges of the A-class of prostaglandins:

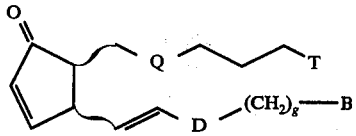

When L is carbonyl, K is methylene or ethylene and J is methylene or hydroxymethylene such that K is ethylene only when J is methylene, III represents analogues of the E-class, 11-deoxy-E- class or 9a-homo-11-deoxy-E-class of prostaglandins:

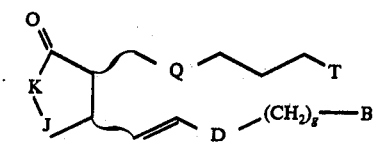

When L is carbonyl, K is methylene and J is R-hydroxymethylene or S-hydromethylene, III represents analogues of the E-class of prostaglandins:

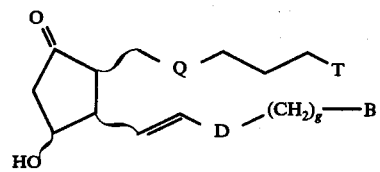

When L is carbonyl and both J and K are methylene, III represents analogues of the 11-deoxy-E-class of prostaglandin:

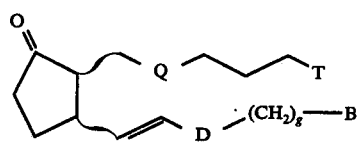

When Q is Z-vinylene, L is carbonyl, K is ethylene and J is methylene, III represents analogues of 9a- omo-11-deoxy-PGE₂:

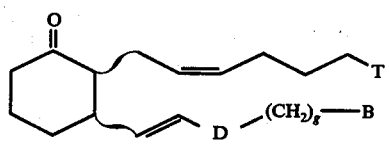

When L is R-hydroxymethylene or S-hydroxymethylene; K is methylene or ethylene; J is R-hydroxymethylene, S-hydroxymethylene or methylene such that K is ethylene only when J is methylene, III represents analogues of PGF₃, PGF_β, 11-deoxy-F_α, 11-deoxy-F_β, 9a-homo-11-deoxy F_α and 9a-homo-11-deoxy F_β:

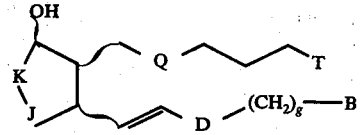

When L is R-hydroxymethylene or S-hydroxymethylene; K is methylene; and J is R-hydroxymethylene or S-hydroxymethylene, III represents analogues of PGF_α and PGE_β:

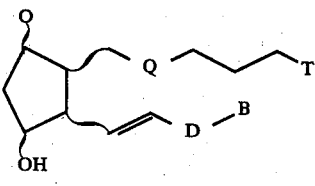

Useful intermediates in the preparation of compounds of Formula III are represented by the formula:

 (IV)

wherein:
X is an iodo or bromo radical;
A is an acid-labile protecting group selected from the class consisting of 1-ethoxyethylene, trimethylsilyl, tert-butyl-dimethylsilyl, 2-ethoxy-prop-2-yl, triphenyl-methyl, or tetrahydropyran-2-yl radicals;
g is an integer having a value of from 0 to 10; and
B is selected from the class of bicycloalkyl radicals of the formula:

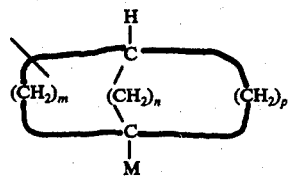

where $m$ and $p$ are integers having a value of from 1 to 4; $n$ is an integer having a value of from 0 to 4 such that the sum of $m$, $n$ and $p$ is greater than or equal to 3 and the point of attachment of the alkyl chain $(CH_2)_g$ to the bicycloalkyl radical is in the $(CH_2)_m$ bridge or in the bridgehead position.

Other useful intermediates in the preparation of compounds of Formula III are represented by the formula:

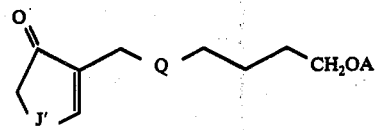

wherein:
A is an acid-labile hydroxyl-protecting group selected from the class consisting of 1-ethoxyethylene, trimethylsilyl, tert-butyl-dimethylsilyl, 2-ethoxy-prop-2-yl, triphenyl methyl, or tetrahydropyran-2-yl radicals;
Q is an ethylene or Z-vinylene radical; and
J' is a R-hydroxymethylene radical protected with an acid-labile hydroxyl-protecting group A.

Another useful intermediate in the preparation of compounds of Formula III is methyl 7-(6-oxocyclohex-1-enyl) hept-5Z-enoate.

DESCRIPTION OF THE INVENTION

Compounds having Formula III are prepared via the 1,4-conjugate addition of organocopper reagents to cyclopentenones as reported by Sih, et. al., (J.Amer. Chem. Soc., 97: 857,865 (1975) and references cited therein). The novel compounds of Formula III are prepared according to the reaction sequence depicted in Table A.

TABLE A

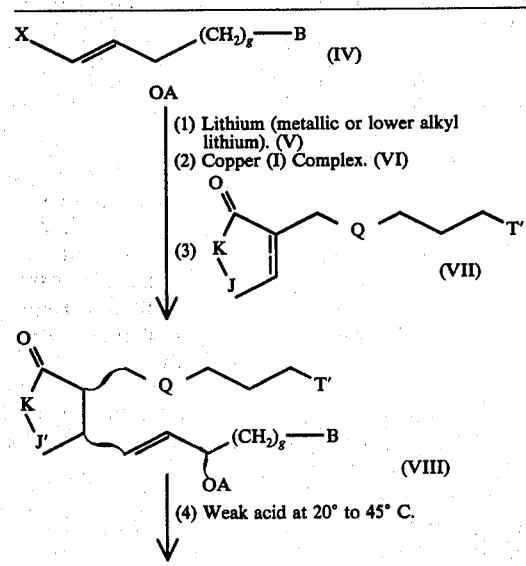

TABLE A-continued

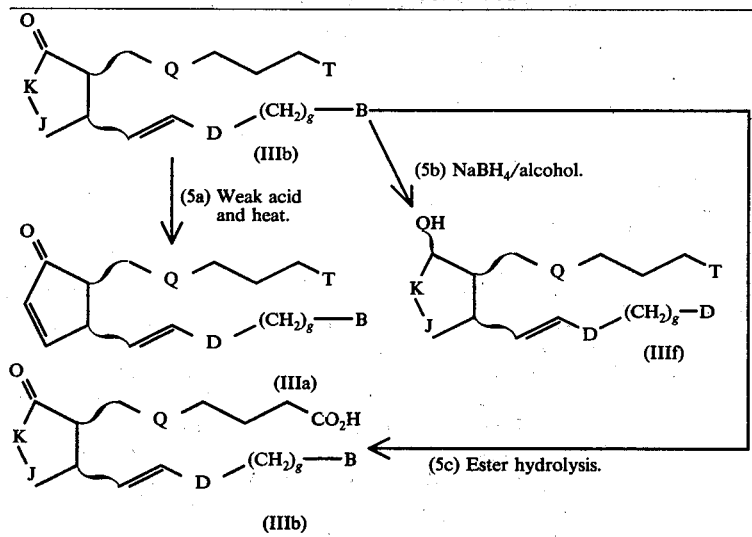

In Table A, Compound IV, where X is an iodo or bromo radical and A is an acid-labile hydroxyl-protecting group, is contacted and reacted with metallic lithium or a lower alkyl lithium (Compound V) at from about −80° C to 0° C for about 0.25 to 3.0 hours in an inert solvent, such as ether, tetrahydrofuran, hexane., pentane, toluene, mixtures thereof and the like, under an inert atmosphere, such as argon, nitrogen and the like. Copper(I) complex (Compound VI) is added, usually as a solution in an inert solvent, to the reaction mixture and the mixture is then stirred at less than about −20° C for about 0.25 to 1.0 hour. A solution of Compound VII, where J' is methylene or =CHOA and T' is alkoxycarbonyl or —CH$_2$OA, usually in an inert solvent, is added to the reaction mixture which is then allowed to warm to about −20° C to 25° C over a 0.5 to 5 hour period to yield the intermediate Compound VIII after quenching with a proton donor. Treatment of the latter compound under hydrolysis conditions such as with a weakly-acidic water mixture, such as acetic acid-water (65:35 V/V) with 10% tetrahydrofuran, under an inert atmosphere at a temperature of about 20° C to 45° C for about 0.5 to 48 hours cleaves the acid-labile hydroxyl-protecting groups (described in J. Amer. Chem. Soc., 94:6194[1972]) to yield Compound IIIb.

Where J and K of Compound IIIb are respectively hydroxymethylene and methylene, dehydration of Compound IIIb with a weakly-acidic water mixture, such as acetic acid-water, at about 60° C to 80° C (described in J. Org. Chem., 34:3552 [1969]) yields Compound IIIa, Compound IIIa is also obtained as a by-product of the acidic hydrolysis of Compound VIII.

Reduction of Compound IIIb with sodium borohydride in an inert alcoholic or other suitable polar solvent (described in J. Org. Chem., 34:3552[1969]) yields Compound IIIf.

When T of Compound IIIb (where J is methylene or IIIf is alkoxycarbonyl, cleavage of the ester group with a base, such as sodium hydroxide or potassium hydroxide in a mixed organic solvent such as water-tetrahydrofuran, water-p-dioxane or water-alcohol described in J. Amer. Chem. Soc., 94:7823 [1973]) yields the corresponding acid, i.e. where T is carboxyl. Where J and T of Compound IIIb are respectively hydroxymethylene and alkoxycarbonyl, cleavage of the ester group by exposure to Rhizopus oryzae (described in J. Amer. Chem. Soc. 95:1676[1973]) or with a suitable esterase or lipase (described in U.S.P.N. 3,769,166 and German Patent Application No. 2,242,792) yields the corresponding acid, i.e. where T is carboxyl.

Where T of Compounds IIIa, IIIb or IIIf is a carboxyl or alkoxycarbonyl group, reduction of the carboxyl or ester group, after treatment with a carboxyl protecting group, followed by treatment with nitrous acid yields the corresponding primary alcohol, ie. where T is hydroxymethyl (described in U.S. Pat. No. 3,636,120). Suitable carboxyl protecting groups include lower alkoxyamines, semicarbazides or thiosemicarbazides. Suitable reducing agents include lithium aluminum hydride, lithium borohydride, or diisobutyl aluminum hydride.

Non-toxic, pharmacologically acceptable salts of Compound III can be prepared by neutralization of III, where T is carboxyl, with an equivalent or an excess amount of the corresponding non-toxic salt-forming organic or inorganic base. The salts are prepared by procedures which are well-known in the art. Suitable salts include sodium, potassium, ammonium and the like. The salts may be isolated by lyophilization of the resulting mixture, or by filtration, if sufficiently insoluble, or by similar well-known techniques.

All compounds of this invention can be isolated from reaction mixtures and purified by well-known organic chemistry procedures. For example, the compounds can be isolated by dilution of the reaction mixture with water, extraction with a water-immiscible solvent such as benzene, cyclohexane, ether, ethyl acetate, methylene chloride, toluene and the like; chromatography; distillation or a combination of these procedures. Purification of these compounds can be accomplished by methods which are well-known in the art for the purification of prostaglandins, lipids, fatty acids, and fatty esters. For example, such methods as reverse phase partition chromatography; counter-current distribution; adsorption chromatography on acid washed magnesium silicate, neutral or acid washed silica gel, alumina or silicic acid; preparative paper chromatography; preparative thin layer chromatography; high pressure liquid-liquid chromatography; gas-liquid chromatography;

and combinations thereof can be used to purify the compounds produced by the processes of this invention.

The starting reactants used in the above procedures are well-known or easily prepared by known methods. For instance, in the reaction sequence depicted in Table A, Compound V, i.e. metallic lithium or lower alkyl lithium such as t-butyllithium, sec-butyllithium or n-butyllithium are commercially available or prepared by well-known organic chemistry methods. Examples of Compound VI, i.e. copper(I) complexes, include: [hexamethylphosphorous triamide]$_2$ copper(I) pentyne (preparation described in J. Amer. Chem. Soc., 94:7210[1972]; and J. Org. Chem., 31:4071[1966]); tri-n-butylphosphine-copper(I) iodide (preparation described in Inorg. Synth., 7:9]1963]); hexamethylphosphorous triamide-copper(I) iodide (preparation described in Prostaglandins, 7:387[1974]); copper(I) thiophenolate (preparation described in Synthesis, 662[1974]) and the like. Examples of Compound VII which are employed in the synthesis of III include: methyl 7-(5-oxocyclopent-1-enyl)heptanoate (preparation described in Tet. Let., 24:2435[1972]); methyl 7-[3R-(tetrahydropyran-2-yloxy)-5-oxocyclopent-1-enyl]heptanoate (preparation described in J. Amer. Chem. Soc., 95:1676[1973]); 1-(tetrahydropyran-2-yloxy)-7-(5-oxocyclopent-1-enyl)-heptane (preparation described in Tet. Let., 773[1972]); Methyl 7-(5-oxocyclopent-1-enyl)hept-5Z-enoate (preparation described in J. Org. Chem., 38:3413[1973]); Methyl 7-[3R-(tetrahydropyran-2-yloxy)-5-oxocyclopent-1-enyl]hept-5Z-enoate (preparation described in Tet. Let., 2313[1973]); Methyl 7-(6-oxocyclohex-1-enyl)hept-5Z-enoate (preparation of this novel compound is described in Example 13); 1-(tetrahydropyran-2-yloxy(-7-[3R-(tetrahydropyran-2-yloxy)-5-oxocyclopent-1-enyl]heptane (TR-C7E1).; and 1-(tetrahydropyran-2-yloxy)-7-[3R-(tetrahydropyran-2-yloxy)-5-oxocyclopent-1-enyl]hept-5Z-ene (TR-C7E2).

Compounds TR-C7E1 and TR-C7E2, disclosed above, are novel intermediates useful in the preparation of prostaglandin analogues of the $E_1$ and $E_2$ classes where T is a hydroxymethyl radical in Formula IIIc. Compounds TR-C7E1 and TR-C7E2 can be prepared from well-known materials by the following reaction scheme:

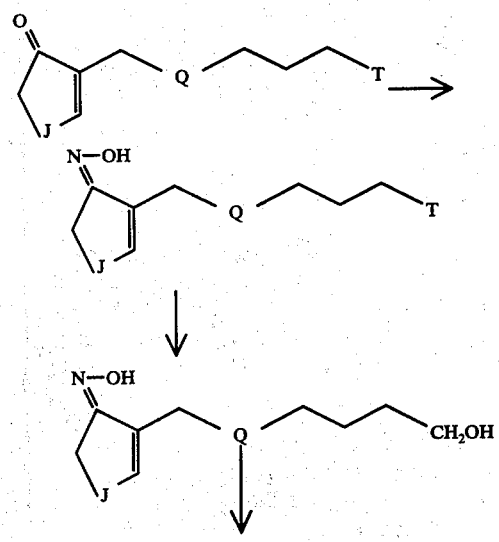

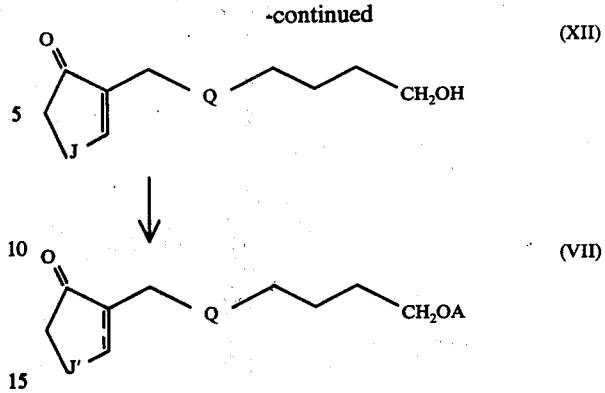

wherein J is a R-hydroxymethylene radical; Q is an ethylene or Z-vinylene radical; T is an alkoxycarbonyl, having from 1 to 3 carbon atoms inclusive in the alkyl chain, or carboxyl radical; A is an acid-labile hydroxyl-protecting group; and J' is an R-hydroxymethylene radical protected with an acid-labile hydroxyl-protecting group A. In IX → X, Compound IX is reacted with hydroxylamine to form the corresponding oxime-protected carbonyl, Compound X, using conditions which are well-known in the art (see U.S. Pat. No. 3,636,120 and Australian Patent No. 5,108,173). In X → XI, Compound X is reacted with a suitable reducing agent such as lithium aluminum hydride, lithium borohydride, diisobutyl aluminum hydride and the like, at a temperature below about 30° C. to reduce the ester or carboxyl group at T to the corresponding alcohol, Compound XI (where T is hydroxymethyl). In XI → XII, Compound XI is reacted with nitrous acid at a temperature of about −10° C to about 50° C to remove the oxime protecting group and regenerate the carbonyl. The nitrous acid is formed by adding an aqueous solution of an alkali metal or alkaline earth metal nitrite, such as sodium nitrite, to a liquid alkanoic acid such as acetic or propionic acid. In XII → VII, Compound XII is reacted with a suitable acid-labile hydroxyl-protecting groups (A) such as dihydropyran or ethylvinyl ether in the presence of an acid catalyst such as p-toluensulfonic acid, 98% sulfuric acid or phosphorus oxychloride to form Compound VII and the product is isolated by standard procedures.

Compound IV of Table A is prepared according to the reaction sequence depicted in Table B. Examples of compounds having Formula IV which are used in the reaction IV → III include: 1-iodo-3-(1-ethoxyethoxy)-3-(bicyclo[3.2.0]hept-3-yl)-1E-propene; 1-iodo-3-(1-ethoxyethoxy)-7-(bicyclo[3.2.1]oct-2-yl)-1E-heptene; 1-iodo-3-(1-ethoxyethoxy)-7-(bicyclo[4.4.0]dec 2-yl)-1E-heptene and 1-iodo-3-(1-ethoxyethoxy)-4-(bicyclo[2.2.1]hept-2-yl)-1E-butene. The synthesis of Compound IV from the corresponding bicycloalkyl acid IVa can be accomplished via the reaction sequence of Table B by well-known organic chemistry procedures.

TABLE B

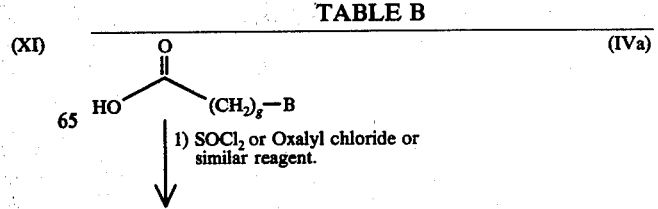

1) SOCl$_2$ or Oxalyl chloride or similar reagent.

TABLE B-continued

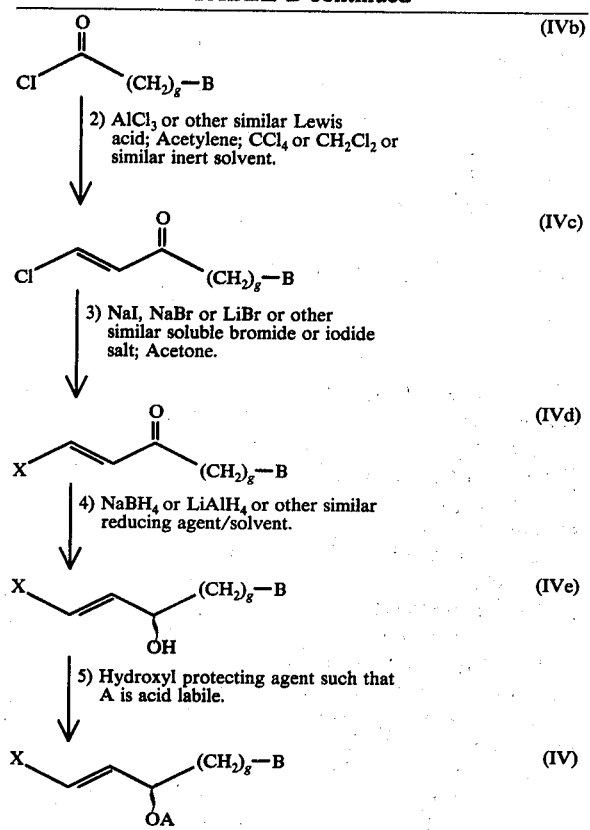

In IVa → IVb, the bicycloalkyl acid IVa is converted to the acid chloride IVb using an acid chloride forming reagent such as thionyl chloride, oxalyl chloride, phosphorus trichloride and the like as described in Fieser & Fieser, Reagents For Organic Synthesis, I: 1158, J. Wiley & Sons Inc. (1967). In IVb → IVc, the acid chloride IVb is reacted with acetylene in an inert solvent, such as carbon tetrachloride, methylene chloride or the like, in the presence of a Lewis acid such as aluminum chloride, stannic chloride or the like to produce the β-chlorovinyl ketone IVc as described in Chem. Rev., 161(1965) and Org. Synth., IV:186, J. Wiley & Sons Inc. (1963). In IVc → IVc, the β-chlorovinyl ketone IVc is converted into the corresponding β-iodo- or β-bromovinyl ketone IVd, where X is an iodo or bromo radical, using a soluble salt, such as sodium iodide, sodium bromide, lithium bromide or the like, in a polar inert solvent, such as acetone, acetonitrile or the like, as described in J. Amer. Chem. Soc., 94:7210(1972). In IVd → IVe, Compound IVd is reduced to the corresponding β-iodo- or β-bromo-vinyl alcohol using a suitable reducing agent, such as sodium borohydride in alcohol solvent or lithium aluminum hydride in ether solvent as described in J. Amer. Chem. Soc., 94:7210(1972). In IVe → IV, Compound IVe is contacted and reacted with a suitable hydroxyl-protecting agent (A) such as dihydropyran or ethylvinyl ether in the presence of an acid catalyst such as p-toluenesulfonic acid, 98% sulfuric acid or phosphorus oxychloride; or a trialkylsilylchloride, such as trimethylsilylchloride or t-butyldimethysilylchloride, or triphenylmethylbromide in the presence of a basic catalyst such as triethylamine or imidazole. Any hydroxyl protecting group that is removable under mildly acid conditions and is stable to alkyllithium and alkylcopper(I) reagents can also be suitably used, see J. Org. Chem. 37:1947(1972).

Examples of the corresponding bicycloalkyl carboxylic acids having Formula IVa include: bicyclo[3.2.0]heptane-3-carboxylic acid; 5-(bicyclo[3.2.1]oct-2-yl)pentanoic acid; 5-(bicyclo[4.4.0]dec-2-yl)pentanoic acid; and (bicyclo[2.2.1]hept-2-yl)acetic acid. The bicycloalkyl carboxylic acids of Formula IVa are either commercially available or are prepared by well-known techniques from commercially available materials. For example, the Compound cis-1,2-cyclobutanedicarboxylic anhydride is reduced with a suitable reagent, such as lithium aluminum hydride, lithium borohydride, lithium tri-t-butoxyaluminum hydride or borane, to produce cis-1,2-bis(hydroxymethyl)cyclobutane. This latter compound is then substituted for trans-1,2-bis-(hydroxymethyl)cyclobutane in the procedure described in J. Org. Chem., 29:2914 (1964) for the preparation of trans-(bicyclo[3.2.0]hept-3-yl)carboxylic acid. The product of this procedure is thus cis-(bicyclo[3.2.0]hept-3-yl)carboxylic acid. This latter compound is used in the reaction sequence depicted in Table B to produce 1-iodo-3-(1-ethoxyethoxy)-3-(bicyclo[3.2.0]hept-3-yl)-1E-propene.

Other commercially available cis or trans isomers of 1,2-dicarboxycycloalkyl; 1,2-bis(hydroxymethyl)cycloalkyl; or 1,2-bis(bromomethyl)cycloalkyl may be used in the above procedure to produce compounds of structure IVa where g is 0 and B is

These latter compounds lead to prostaglandins of structure III in which g is 0, m is 3, n is 0 and p is 1 to 4.

5-(Bicyclo[3.2.1]oct-2-yl)pentanoic acid is prepared by the following procedure. The compound 2-oxobicyclo[3.2.1]octane is reacted with a suitable base, such as sodium hydride, potassium hydride, lithium hydride, lithium diisopropylamide, or lithium t-butoxide, and (4-carboxybutyl)triphenyl phosphonium bromide in an inert solvent such as dimethylsulfoxide, benzene, diethylether, t-butanol or mixtures thereof, via a Wittig reaction (Tet. Let., 4:311 [1970],) to produce the intermediate compound 5-(bicyclo[3.2.1]oct-2-ylidene)pentanoic acid. This latter compound is catalytically reduced in a suitable solvent such as ethanol, other alcohols or organic acids in the presence of a hydrogenation catalyst such as platinum oxide, Pd on carbon, $RuO_2$, or Ra-Ni and a reducing agent such as hydrogen, diimide or the like to produce 5-(bicyclo[3.2.1]oct-2-yl)pentanoic acid. This latter compound is used in the reaction sequence depicted in Table B to produce 1-iodo-3-(1-ethoxyethoxy)-7-(bicyclo[3.2.1]oct-2-yl)-1E-heptene.

Other commercially available or easily prepared oxobicyclo[m.n.p]alkanes can be used in place of 2-oxobicyclo[3.2.1] octane in the Wittig reaction to yield a variety of 5-(bicyclo[m.n.p]alkylidene) pentanoic acids which can then be used in the synthesis of a variety of prostaglandins with structure III. For example, cis or trans (bicyclo[4.4.0] decan-1-one) may be used in the above Wittig reaction followed by reduction to produce 1-iodo-3-(1-ethoxyethoxy)-7-bicyclo[4.4.0]dec-2-yl)-1E-heptene.

Easily prepared (ω-carboxylkyl) triphenyl phosphonium bromide reagents may be used in place of (4-carboxybutyl) triphenyl phosphonium bromide in the Wittig reaction to yield ω-(bicyclo[m.n.p.]alkylidene) alkanoic acids which can then be used in the synthesis of prostaglandins with Structure III. The (ω-carboxyalkyl)triphenyl phosphonium bromide reagents are most easily prepared by reacting triphenylphosphine with an ω-bromoalkanoic acid in an inert solvent such as benzene, acetonitrile, ether or the like, usually at an elevated temperature, such as solvent reflux. The products are usually isolated as crystalline salts which separate from the reaction mixture upon cooling.

The compounds represented by Formula III inhibit aggregation of human platelets in vitro as demostrated in the following Example 14. It is that feature which distinguishes the compounds of this invention over the natural prostaglandins. Of the natural prostaglandins, only $PGE_1$ displays a similar activity. The protaglandin analogues of this invention also stimulate in vitro and in vivo smooth muscle preparations derived from a variety of tissues and organs of experimental animals. Such smooth muscle assays are widely utilized to determine the activity of natural prostaglandins as well as prostaglandin analogues (Bundy et al., Ann. N.Y. Acad. Sci., 180:76[1961]; Bergstrom et al., Pharmacol. Revs., 20:1[1968]). Details of the activity of certain compounds having Formula III are presented in Example 14 below.

The following Table C illustrates preferred embodiments of the present invention compiled by Compound No., Example No. and identified by both the I.U.P.A.C. and Nelson systems of nomenclature.

TABLE C

| Compound No. | Ex. No. | IUPAC Nomenclature | Nelson System |
|---|---|---|---|
| TR-4118 | 2D | methyl 7-{5-oxo-2R-[3S-hydroxy-7-(bicyclo-[3.2.1]oct-2-yl)-1E-heptenyl]cyclopent-3-en-1R-yl}heptanoate. | 19-(bicyclo[3.2.1]oct-2-yl)-20-norprostaglandin $A_1$ methyl ester |
| TR-4119 | 2C | methyl 7-{5-oxo-2R-[3R-hydroxy-7-(bicyclo-[3.2.1]oct-2-yl)-1E-hepentyl]cyclopent-3-en-1R-yl}heptanoate. | 15-epi-19-[bicyclo[3.2.1 oct-2-yl)-20-norprostaglandin $A_1$ methyl ester |
| TR-4098 | 1A | methyl 7-{3R-hydroxy-5-oxo-2R-[3R-hydroxy-3-(bicyclo[3.2.0]hept-3-yl)-1E-propenyl]-cyclopent-1R-yl]heptanoate. | 15-(bicyclo[3.2.0]hept-3-yl)-16,17,18,19,-20-pentanor prostaglandin $E_1$ methyl ester |
| TR-4099 | 1B | methyl 7-{3R-hydroxy-5-oxo-2R-[2S-hydroxy--3-(bicyclo[3.2.0]hept-3-yl)-1E-propenyl]-cyclopent-1R-yl)heptanoae. | 15-epi-15-(bicyclo[3.2.0]hept-3-yl)-16,17,-18,19,20-pentanor prostaglandin $E_1$ methyl |
| TR-4117 | 2A | methyl 7-{3R-hydroxy-5-oxo-2R-[3S-hydoxy-7-(bicyclo[3.2.1]oct-2-yl)-1E-heptenyl]-cyclopent-1R-yl}heptanoate. | 19(bicyclo[3.2.1]oct-2-6l)-20-norprostaglandin $E_1$ methyl ester |
| TR-4116 | 2B | methyl 7-{3R-hydroxy-5-oxo-2R-[3R-hydroxy-7-(bicyclo[3.2.1]oct-2-yl)-1E-heptenyl]-cyclopent-1R-yl}heptanoate. | 15-epi-19-(bicyclo[3.2.1]oct-2-yl)-20-norprostaglandin $E_1$ methyl ester |
| TR-4172 | 2E | methyl 7-{3R-hydroxy-5-oxo-2R-[3S-hydroxy-8-(bicyclo[4.4.0]dec-2-yl)-1E-heptenyl[cyclopent-1R-yl)heptanoate. | 19-(bicyclo[4.4.0]dec-2-yl)-20-norprostaglandin $E_1$ methyl ester |
| TR-4166 | 2F | methyl 7-55 3R-hydroxy-5-oxo-2R-[3R-hydroxy-7-{3R-hydroxy-5-oxo-2R-[3R-hydroxy-7-(bicyclo[4.4.0]dec.-2-yl)-1E-heptenyl]cyclopent-1R-yl}heptanoate. | 15-epi-19-(bicyclo[4.4.0]dec-2-yl)-20-15-epi-19-(bicyclo[4.4.0]dec-2-yl)-20-norprostaglandin $E_1$ methyl ester |
| TR-4643 | 3A | 7-{3R-hydroxy-5-oxo 2R-[3S-hydroxy-3-(bicyclo[3.2.0]hept-3-yl)-1E-propenyl]-cyclopent-1R-yl}heptan-1-ol. | 15-epi-15-(bicyclo[3.2.0]hept-3-yl)-2-decarboxy-2-hydroxymethyl-16,17,18,19,20-pentanorprostagland $E_1$ |
| TR-4642 | 3B | 7-{3R-hydroxy-5-oxo-2R-[3R-hydroxy-3-(bicyclo[3.2.0]hept-3-yl)-1E-propenyl]-cyclopent-1R-yl}heptan-1-ol. | 15-(bicyclo[3.2.0]hept-3-yl)-2-decarboxy-2-hydroxymethyl-16,17,18,19,20-pentanorprostaglandin $E_1$ |
| TR-4097 | 4A | dl-7-{5-oxo-2R-[3S-hydroxy-3-(bicyclo-[3.2.0]hept-3-yl)-1E-propenyl]cyclopent-1R-yl}heptanoic acid. | (+)-11-deoxy-15-epi-15-(bicyclo[3.2.0]hept-3-yl)-16,17,18,19,20-pentanorprostaglandin $E_1$ |
| TR-4096 | 4B | dl-7-{5-oxo-2R[3R-hydroxy-3-(bicyclo-[3.2.0]hept-3-yl)-1E-propenyl[cyclopent-1R-yl}heptanoic acid. | (+)-11-deoxy-15-(bicyclo[3.2.0]hept-3-yl)-16,17,18,19,20-pentanoprostaglandin $E_1$ |
| TR-4189 | 5A | dl-7-{5-oxo-2R[3S-hydroxy-7-(bicyclo-[4.4.0]dec-2-yl)-1E-heptenyl]cyclopent-1R-yl}heptanoic acid. | (+)-11-deoxy-19-(bicyclo[4.4.0]dec-2-yl)-20-norprostaglandin $E_1$ |
| TR-4190 | 5B | dl-7-{5-oxo-2R-[3R-hydroxy-7-(bicyclo-[4.4.0]dec-2-yl)-1E-heptenyl]cyclopent-1R-yl}heptanoic acid. | (+)-11-deoxy-15-epi-19-(bicyclo[4.4.0]dec-2-yl)-20-norprostaglandin $E_1$ |
| TR-4101 | 6A | dl-7-{5-oxo-2R[3R-hydroxy-2-(bicyclo-[3.2.0]hept-3-yl)-1E-propenyl]cyclopent-1R-yl}hept-5Z-enoic acid. | (+)-11-deoxy-15-(bicyclo[3.2.0]hept-3-yl)-16,17,18,19,20-pentanorprostaglandin $E_2$ |
| TR-4102 | 6B | dl-7-{5-oxo-2R-[8 3S-hydroxy-3-(bicyclo-[3.2.0]hept-3-yl)-1E-propenyl]cyclopent-1R-yl]hept-5Z-enoic acid. | (+)-11-deoxy-15-epi-15-(bicyclo[3.2.0]hept-3-yl)-16,17,18,19,20-pentanorprostaglandin $E_2$ |
| TR-4173 | 6C | dl-7-{5-oxo-2R-[3R-hydroxy-7-(bicyclo-[4.4.0]dec-2-yl)-1E-heptenyl]cyclopent-1R-yl}hept-5Z-enoic acid. | (+)-11-deoxy-19-(bicyclo[4.4.0]dec-2-yl)-20-norprostaglandin $E_2$ |
| TR-4174 | 6D | dl-7-{5-oxo-2R-[3R-hydroxy-7-(bicyclo-[4.4.0]dec-2-yl)-1E-heptenyl]cyclopent-1R-yl}-hept-5Z-enoic acid. | (+)-11-deoxy-15-epi-19-(bicyclo[4.4.0]dec-2-yl)-20-norprostaglandin $E_2$ |
| TR-VIIa | 7A | dl-7-{6-oxo-2R-[3S-hydroxy-7-(bicyclo-[4.4.0]dec-2-yl)-1E-heptenyl]cyclohex-1R-yl}hept-5Z-enoic acid. | (+)-11-deoxy-19-(bicyclo[4.4.0]dec-2-yl)-9a-homo-20-norprostaglandin $E_2$ |
| TR-VIIb | 7B | dl-7-{6-oxo-2R-[3R-hydroxy-7-(bicyclo-[4.4.0[dec-2-yl)-1E-heptenyl]cyclohex-1R-yl}hept-5Z-enoic acid. | (+)-11-deoxy-15-epi-19-(bicyclo[4.4.0]dec-2-yl)-9a-homo-20-norprostaglandin $E_2$ |
| TR-4712 | 8A | methyl 7-{3R,5R-dihydroxy-2R-[3S-hydroxy-3-(bicyclo[3.2.0]hept-3-yl)-1E-propenyl]-cyclopent-1R-yl}heptanoate. | 15-epi-15-(bicyclo[3.2.0]hept-3-yl)-16,17,-18,19,20-pentanorprostaglandin $F_{1\beta}$ methyl ester |
| TR-4711 | 8B | methyl 7-{3R, 5S-dihydroxy-2R-[3S-hydroxy-3-(bicyclo[3.2.0]hept-3-yl)-1E-propenyl]-cyclopent-1R-yl}heptanoate. | 15-epi-15-(bicyclo[3.2.0]hept-3-yl)-16,17,-18,19,20-pentanorprostaglandin $F_{1\alpha}$ methyl ester |

In order to further illustrate the novel aspects of the present invention, the following examples are presented. It should be recognized that these examples are provided by way of illustration only and are not intended to limit in any way the invention disclosed herein. Compounds identified by compound number in the following examples refer to the compounds as compiled in Table C.

EXAMPLE 1

This example illustrates a typical preparation of Prostaglandin $E_1$ Analogues.

Compounds TR-4098 and TR-4099 were prepared according to the procedure which follows. A mixture containing 940 mg (3.14 mmol) of 1-iodo-3-(1-ethoxyethoxy)-3-(bicyclo[3.2.0]hept-3-yl)-1E-propene (see Example 11) dissolved in 180 ml of ether was prepared, cooled to −78° C, and stirred under an argon atmosphere. Then 3.38 ml of 1.7N t-butyllithium in n-pentane was added and the mixture was stirred at a temperature of −78° C for 2 hr. A solution of 328 mg of copper(I) pentyne and 0.9 ml hexamethyl phosphorous triamide in 10 ml ether was added to the reaction flask with stirring at −78° C. The resulting mixture was stirred 40 min at −78° C, and 714 mg (2.20 mmol) of methyl 7-[3R-tetrahydropyran-2-yloxy)-5-oxocyclopent-1-enyl]heptanoate in 6.0 ml of ether was added thereto. The mixture was stirred for 35 min at −78° C and subsequently brought to −10° C and stirred for 1.5 hr. The mixture was stirred for 0.5 hr at 0° C and an additional 0.5 hr at 25° C. The mixture was quenched by the addition of 20% aqueous ammonium sulfate and extracted with ether. The ether extract was shaken successively with 2% (v/v) sulfuric acid, saturated aqueous $NaHCO_3$, saturated aqueous NaCl, then dried over $MgSO_4$, filtered through diatomaceous earth and the solvents removed in vacuo to yield 1.40 g of a yellow oil. The resulting oil was stirred with 27.0 ml of 65:35 acetic acid-water and 2.7 ml of tetrahydrofuran for 15 hr at 25° C. The solvents were removed in vacuo and the residue was mixed with water and extracted several times with ether. The ether extracts were washed with aqueous sodium bicarbonate and then aqueous saturated NaCl. The washed ether extracts were then dried over $MgSO_4$ and evaporated in vacuo to yield 1.30 g of a yellow oil. The oil was column chromatographed using an 85:15 silicic acid:diatomaceous earth (Celite) support and using a benzene to ethyl acetate gradient elution to yield 126.4 mg of Compound TR-4098 and 155 mg of Compound TR-4099.

A. Compound TR-4098 had the following spectral properties:

Analysis — IR: $\lambda_{max}^{CHCl_3}$ 2.78μ, 2.90μ, 5.75μ and 10.30μ

NMR($CDCl_3$) δ3.67, singlet, 3H, $CO_2CH_3$ δ4.05, multiplet, 2H, CHOH δ5.82, multiplet, 2H, trans-olefinic-H Optical Rotation: $[\alpha]_D$(CHCl$_3$, c 1.02): −55.4°.

B. Compound TR-4099 had the following spectral properties:

Analysis — IR: $\lambda_{max}^{CHCl_3}$ 2.78μ, 2.90μ, 5.75μ and 10.30μ.

NMR($CDCl_3$) δ3.67, singlet, 3H, $CO_2CH_3$, δ4.05, multiplet, 2H, CHOH, δ5.82, multiplet, 2H, trans-olefinic-H.

Optical Rotation: $[\alpha]_D$(CHCl$_3$, c 1.00): −49.0°.

EXAMPLE 2

This example illustrates the preparation of other Prostaglandin $E_1$ Analogues and Prostaglandin $A_1$ Analogues.

Repeating in a similar manner the procedure of Example 1, but replacing 1-iodo-3-(1-ethoxyethoxy)-3-(bicyclo[3.2.0]hept-3-yl)-1E-propene with 1-iodo-3-(1-ethoxyethoxy)-7-(bicyclo[3.2.1]oct-2-yl)-1E-heptene (see Example 9) or 1-iodo-3-(1-ethoxyethoxy)-7-(bicyclo[4.4.0]dec-2-yl)-1E-heptene (see Example 10) yields the following $PGE_1$ and $PGA_1$ analogues.

A. Compound TR-4117 had the following spectral properties:

Analysis — IR: $\lambda_{max}^{CHCl_3}$ 2.78μ, 2.90μ, 5.75μ and 10.30μ

NMR($CDCl_3$): δ3.67, singlet, 3H, $CO_2CH_3$ δ4.1, multiplet, 2H, CHOH δ5.66, multiplet, 2H, trans-olefinic-H.

Optical Rotation: $[\alpha]_D$(CHCl$_3$, c 0.94): −29.3°.

B. Compound TR-4116 had the following spectral properties:

Analysis — IR: $\lambda_{max}^{CHCl_3}$ 2.78μ, 2.90μ, 5.75μ 10.30μ

NMR($CDCl_3$): δ3.64, singlet, 3H, $CO_2CH_3$ δ4.1, multiplet, 2H, CHOH δ5.66, multiplet, 2H, trans-olefinic-H Optical Rotation: $[\alpha]_D$(CHCl$_3$, c 1.03): −21.0°.

Compounds TR-4119 and TR-4118, Prostaglandin $A_1$ analogues, are formed in the preparation of Compounds TR-4117 and TR-4116 above as side products by the treatment with 65:35 acetic acid-water.

C. Compound TR-4119 has the following spectral properties:

Analysis — IR: $\lambda_{max}^{CHCl_3}$ 2.78μ, 2.88μ, 5.78μ, 5.88μ, 6.30μ and 10.08μ

NMR($CDCl_3$): δ3.67, singlet, 3H, $CO_2CH_3$ δ3.30, multiplet, 1H, $C_{12}$-H δ4.12, multiplet, 1H, $C_{12}$-H δ5.60, multiplet, 2H, trans-olefinic-H δ6.17 (dd, J=2.0, 5.0Hz, 1H, $C_{10}$-H δ7.46 ppm (dd, J=2.0, 5.0Hz, 1H, $C_{11}$-H)

Optical Rotation: $[\alpha]_D$(CHCl$_3$, c 1.40): +90.0°.

D. Compound TR-4118 had the following spectral properties:

Analysis: spectral similar in essential aspects as those of Compound TR-4119 above.

Optical Rotation: $[\alpha]_D$(CHCl$_3$, c 1.13): +94.7°.

E. Compound TR-4172 had the following spectral properties:

Analysis — IR: $\lambda_{max}^{CHCl_3}$ 2.79–3.03μ, 3.42μ, 5.78μ

NMR($CDCl_3$): δ0.5–3.0, multiplet, 41H δ3.75, singlet, 3H δ3.8–4.3, multiplet, 2H δ5.7, multiplet, 2H Optical Rotation: $[\alpha]_D$(CHCl$_3$, c 1.01): −34.08°.

F. Compound TR-4166 had the following spectral properties:

Analysis — IR: $\lambda_{max}^{CHCl_3}$ 2.79–3.12μ, 3.40μ and 5.78μ

NMR($CDCl_3$): δ0.6–2.8, multiplet, 41H δ3.75, singlet, 3H δ3.7–4.3, multiplet, 2H δ5.7, multiplet, 2H Optical Rotation: $[\alpha]_D$(CHCl$_3$, c 1.56): −21.1°.

EXAMPLE 3

This example illustrates the preparation of other Prostaglandin $E_1$ analogues.

Repeating in a similar manner the procedure of Example 1, but replacing methyl 7-[3R-{3R-(tetrahydropyran-2-yloxy)-5-oxocyclopent-1-enyl]heptanoate with 1-tetrahydropyran-2-yloxy}-7-[3R-(tetrahydropyran-2-yloxy)-5-oxocyclopent-1-enyl]heptane yields the following $PGE_1$ analogues.

A. Compound TR-4643 had the following spectral properties:

Analysis — IR: $\lambda_{max}^{CHCl_3}$ 2.78μ, 3.13μ, 3.40μ, 3.5μ, 5.75μ, 8.0μ, 9.35μ, and 10.31μ

NMR(CDCl$_3$): δ1.0 to 3.0, multiplet, 27H δ3.1, singlet, 3H δ3.66, triplet, J=5Hz, 2H δ4.1, multiplet, 2H δ5.83 ppm, multiplet, 2H.

MS(70eV)m/e:346(p-H$_2$O) 328(p-2H$_2$O) 318, 302, 275, 269(p-C$_7$H$_{11}$) 251(p-C$_7$H$_{11}$-H$_2$O) 233(p-C$_7$H$_{11}$-2H$_2$O)

Optical Rotation: $[\alpha]_D$(CHCl$_3$, c 1.0): −43°.

B. Compound TR-4642 had the following spectral properties:

Analysis — IR, NMR and MS similar in essential aspects as those of Compound TR-4643 above.

Optical Rotation: $[\alpha]_D$(CHCl$_3$, c 1.0): −28.4°.

EXAMPLE 4

This example illustrates the preparation of Prostaglandin 11-deoxy E$_1$ analogues.

Repeating in a similar manner the procedure of Example 1, but replacing methyl 7-[3R-(tetrahydropyran-2-yloxy)-5-oxocyclopent-1-enyl]heptanoate with methyl 7-(5-oxocyclopent-1-enyl)heptanoate and performing the following additional procedure, to hydrolyze the ester group, yields the following 11-deoxy PGE$_1$ analogues.

Following substantially the procedure of Example 1 as modified above results in the yield of 871 mg of a yellow oil. The yellow oil was stirred with 12.0 ml of 1N NaOH and 12 ml of tetrahydrofuran for 18 hr at 25° C. The solvents were removed in vacuo and the residue was dissolved in water. The water layer was extracted with ethyl acetate and the ethyl acetate extracts were backwashed with water. The aqueous layer was acidified with concentrated hydrochloric acid and extracted with ether. The ether extracts were washed with aqueous saturated NaCl, dried over MgSO$_4$, filtered through diatomaceous earth, and the ether solvent removed in vacuo to yield 548 mg of oily yellow prisms. This material was chromatographed on 85:15 silicic acid: diatomaceous earth (Celite) using a benzene to ethyl acetate gradient elution to yield 88 mg of Compound TR-4097 and 142 mg of Compound TR-4096.

A. Compound TR-4097 had the following spectral properties:

Analysis — IR: $\lambda_{max}^{CHCl_3}$ 2.78μ, 2.7–4.2μ, 5.85μ, 5.79μ, and 10.03μ

NMR(CDCl$_3$): δ4.0, multiplet, 1H, CHOH δ5.66, multiplet, 2H, trans-olefinic-H δ7.0, broad singlet, 2H, CO$_2$H, OH.

B. Compound TR-4096 had the following spectral properties:

Analysis — IR: $\lambda_{max}^{CHCl_3}$ 2.78μ, 2.7–4.2μ, 5.85μ, 5.79μ, and 10.03μ

NMR(CDCl$_3$): δ3.98, multiplet, 1H, CHOH δ5.65, multiplet, 2H, trans-olefinic-H δ7.35, multiplet, 2H, CO$_2$H, OH.

EXAMPLE 5

Repeating in a similar manner the procedures of Example 1 and 4, but replacing 1-iodo-3-(1-ethoxyethoxy)-3-(bicyclo[3.2.0]hept-3-yl)-1E-propene with 1-iodo-3-(1-ethoxyethoxy)-7-(bicyclo[4.4.0]dec-2-yl)-1E-heptene yields the following 11-deoxy PGE$_1$ analogues.

A. Compound TR-4189 had the following spectral properties:

Analysis — IR: $\lambda_{max}^{CHCl_3}$ 3.41μ, 5.74μ and 5.79μ δ0.7–2.7, multiplet, 43H δ3.65, singlet, 3H δ4.1, multiplet, 1H δ5.5 ppm, multiplet, 2H.

B. Compound TR-4190 had the following spectral properties:

Analysis — IR: $\lambda_{max}^{CHCl_3}$ 3.41μ, 5.74μ, and 5.79μ

NMR(CDCl$_3$): δ0.5–2.8, multiplet, 43H δ3.6, singlet, 3H δ4.5, multiplet, 1H δ5.5 ppm, multiplet, 2H.

EXAMPLE 6

This example illustrates the preparation of Prostaglandin 11-deoxy-E$_2$ analogues.

Repeating in a similar manner the procedures of Examples 1, 4, and 5, but replacing methyl 7-(5-oxocylopent-1-enyl)heptanoate with methyl 7-(5-oxocyclopent-1-enyl)hept-5Z-enoate yields the following 11-deoxy PGE$_2$ analogues.

A. Compound TR-4101 had the following spectral properties:

Analysis - IR: $\lambda_{max}^{CHCl_3}$ 2.78μ, 2.7–4.2μ, 5.79μ, 5.85μ, and 10.3μ.

NMR(CDCl$_3$): δ4.3, multiplet, 1H, CHOH δ5.39, multiplet, 2H. cis-olefinic, H δ5.66, multiplet, 2H, trans-olefinic-H δ7.20, singlet, 2H, CO$_2$H, OH.

B. Compound TR-4102 had spectral properties which were similar in essential aspects as those of Compound TR-4101 above.

C. Compound TR-4173 had the following spectral properties:

Analysis - IR: $\lambda_{max}^{CHCl_3}$ 2.78μ, 3.39μ, 5.28μ and 5.81μ

NMR(CDCl$_3$): δ0.6–2.8, multiplet, 39H δ4.15, multiplet, 1H δ5.55, multiplet, 4H δ6.4 ppm, singlet, 2H.

D. Compound TR-4174 had the following spectral properties:

Analysis - IR: $\lambda_{max}^{CHCl_3}$ 2.78μ, 3.41μ, 5.28μ and 5.81μ

NMR(CDCl$_3$): δ0.6–2.7, multiplet, 39H δ4.9, multiplet, 1H δ5.4, multiplet, 4H δ5.4, multiplet, 4H δ6.25 ppm, singlet 2H.

EXAMPLE 7

This example illustrates the preparation of Prostaglandin 9a-homo-11-deoxy-E$_2$ analogues.

Repeating in a similar manner the procedure of Examples 1 and 4, but replacing 1-iodo-3-(1-ethoxyethoxy)-3-(bicyclo[3.2.0]hept-3-yl)-1E-propene with 1-iodo-3-(1-ethoxyethoxy)-7-(bicyclo[4.4.0]dec-2-yl)-1E-heptene and also replacing methyl 7-[3R-(tetrahydropyran-2-yloxy)-5-oxocyclopent-1-enyl]heptanoate with methyl 7-[6-oxocyclohex-1-enyl]hept-5Z-enoate (see Example 13 for preparation) yields the following 9a-homo-11-deoxy-PGE$_2$ analogues.

A. Compound TR-VIIa had the following spectral properties:

Analysis - IR: $\lambda CHCl^{max CHCl}_3$ 2.79μ, 2.90μ, 5.80μ and 10.30μ.

NMR(CDCl$_3$): δ3.66, singlet, 3H, CO$_2$CH$_3$ δ4.14, multiplet, 1H, CHOH δ5.42, multiplet, 2H, cis-olefinic-H δ5.74, multiplet, 2H, trans-olefinic-H.

B. Compound TR-VIIb had spectral properties which were similar in essential aspects as those of Compound TR-VIIa above.

EXAMPLE 8

This example illustrates the preparation of Prostoglandin F analogues.

A solution of 243 mg of TR-4099 (Example 1) in 25 ml of absolute ethanol was stirred with ice bath cooling as 400 mg of sodium borohydride was added. The resultant mixture was stirred with cooling for 1.25 hr before it was quenched by the addition of water and then evaporated in vacuo to remove solvent. The resultant residue was dissolved in ethyl acetate and washed with water. The wash solution was back extracted with ethyl acetate twice. The combined ethyl acetate extracts were dried (MgSO$_4$) and evaporated in vacuo to yield a clear oil. This material was chromatographed on Woelm silica gel (0.032-0.063 mm) using ethyl acetate elution to yield 105 mg of Compound TR-4712 and 67 mg of Compound TR-4711.

A. Compound TR-4712 had the following spectral properties:

Analysis - IR: $\lambda_{max}^{CHCl_3}$ 2.78μ, 2.90μ, 3.42μ, 5.80μ, 6.96μ, 8.00μ and 10.33μ

NMR(CDCl$_3$): δ3.40, singlet, 3H, OH δ3.70, singlet, 3H, CO$_2$CH$_3$ δ4.05, multiplet, 3H, CHOH δ5.77, multiplet, 2H, trans-olefinic-H Optical Rotation: [α]$_D$ (CHCl$_3$, c 1.0): −14.1°.

B. Compound TR-4711 had spectral properties similar in essential aspects to those of Compound TR-VIIIa above. Optical Rotation: [α]$_D$ (CHCl$_3$, c 1.0): +13.7°.

EXAMPLE 9

This example illustrates a typical preparation of the intermediate compound 1-iodo-3RS-(1-ethoxyethoxy)-7-(bicyclo[3.2.1]oct-2-yl)-1-E-heptene.

A. Preparation of 5-(bicyclo[3.2.1]oct-2-ylidene) pentanoic acid.

A mixture of 3.92 g (93 mmol) of sodium hydride (57% oil dispersion) and 30 ml of dry dimethylsulfoxide was heated at 70°-80° under nitrogen until gas evolution ceased (2.5 hr). The mixture was cooled, and 19.7 g (44.3 mmol) of 4-(carboxybutyl)triphenylphosphonium bromide (Aldrich No. 15,794-5) was added, followed by 20 ml of dimethylsulfoxide. The resulting deep red mixture was stirred for 45 min at room temperature under nitrogen before a solution of 5.0 g (40.2 mmol) of bicyclo[3.2.1]octan-2-one (Aldrich No. 11,903-2) in 20 ml of dimethylsulfoxide was added dropwise over 1.75 hr. The resulting mixture was stirred for 16 hr at room temperature before it was quenched by the addition of 125 ml of water. The resulting solution was extracted with three 250 ml portions of ether/ethyl acetate-1:1 (V/V) to remove neutral by products. The remaining aqueous phase was acidified by the addition of 15 ml of concentrated hydrochloric acid and extracted with three 250 ml portions of ether-hexane-1:1 (V/V). These combined acidic ether-hexane extracts were dried (MgSO$_4$), and evaporated in vacuo to yield 6.0 g of crude 5-(bicyclo[3.2.1]oct-2-ylidene)-pentanoic acid as an oil. This oil was purified by chromatography on silica gel 60 (elution with CHCl$_3$ containing 0.5% formic acid) to yield 4.1 g (49%) of pure material as a colorless oil.

Analysis - IR: $\lambda_{max}^{CHCl_3}$ 5.78μ, 3.41μ and 2.86 to 4.17μ(broad).

NMR(DCl$_3$) δ3.0, broad, 1H δ4.9, broad triplet, 1H.

B. Preparation of 5-(bicyclo[3.2.1]oct-2-yl) pentanoic acid.

A solution of 3.4 g (16.3 mmol) of 5-(bicyclo[3.2.1]-oct-2-ylidene)pentanoic acid in 100 ml of absolute ethanol was hydrogenated at 50 psi over 300 mg of platinum oxide in a Parr apparatus. After 1.5 hr hydrogen uptake became slow. After 4 hr the system was flushed with nitrogen, and the catalyst was removed by filtration through diatomaceous earth filter aid (Celite). The filtrate was evaporated in vacuo to yield 3.25 g (96%) of quite pure 5-(bicyclo[3.2.1]oct-2-yl)pentanoic acid as a colorless oil.

Analysis - IR: $\lambda_{max}^{CHCl_3}$ 5.85μ, 3.41μ and 4.17μ(broad)

NMR(CDCl$_3$): δ11.6, broad singlet, 1H.

C. Preparation of 1-chloro-7-(bicyclo[3.2.1]oct2-yl)-1E-hepten-3-one.

A solution of 7.2 g (32 mmol) of 5-(bicyclo[3.2.1]-oct-2-yl)pentanoic acid in 20 ml of thionyl chloride was left overnight at room temperature under nitrogen. The excess thionyl chloride and byproducts were removed by evaporation in vacuo. The resulting acid chloride (7.8 g) was used in the following procedure. A 65 ml portion of carbon tetrachloride in a flask fitted with a gas addition tube, dropping funnel, and mechanical stirrer was saturated at 0° with acetylene which had been passed through an activated aluminum oxide trap followed by two concentrated sulfuric acid traps. A 5.2 g (40 mmol) portion of anhydrous aluminum chloride was added as acetylene was continuously bubbled through the mixture. The above acid chloride was added dropwise followed by a small amount of carbon tetrachloride rinse. Acetylene was bubbled through the resulting mixture for an additional 4 hr. The mixture was then quenched with 150 ml of crushed ice and 75 ml of brine. The layers which resulted were separated. The aqueous layer was extracted with three 75 ml portions of ether. The combined ether extracts were washed with 10% aqueous HCl three times, saturated aqueous sodium bicarbonate three times, dried (MgSO$_4$), and evaporated in vacuo to yield 8.8 g of residue which was chromatographed on silica gel (benzene elution) to give 3.2 g (37%) of pure 1-chloro-7-(bicyclo[3.2.1]oct-2-yl)-1E-hepten-3-one:

Analysis - NMR(CDCl$_3$): δ2.5, broad t, J=6.5Hz, 2H δ6.48, doublet, J=13.5Hz, 1H δ7.28, doublet, J=13.5Hz, 1H.

D. Preparation of 1-iodo-7-(bicyclo[3.2.1]oct-2-yl)-1E-hepten-3-one.

A solution of 3.2 g (13 mmol) of 1-chloro-7-bicyclo[3.2.1]oct-2-yl)-1E-heptene-3-one and 7.5 g (50 mmol) of sodium iodide in 25 ml of dry acetone (distilled from potassium carbonate) was refluxed for 18 hr under nitrogen. The solvent was removed in vacuo, and the residue was taken up in 50 ml of water and then extracted three times with 30 ml portions of ether. The combined ether extracts were washed with aqueous sodium thiosulfate, dried (MgSO$_4$) and evaporate in vacuo to yield 3.8 g (88%) of 1-iodo-7-(bicyclo[3.2.-1]oct-2-yl)-1E-hepten-3-one.

Analysis - NMR(CDCl$_3$): δ2.5, broad t, J=6.7Hz, 2H δ7.08, doublet, J=15Hz, 1H δ7.78, doublet, J=15Hz, 1H.

E. Preparation of 1-iodo-7-(bicyclo[3.2.1]oct-2-yl)-1E-hepten-3RS-ol.

To a solution of 3.8 g (10.9 mmol) of 1-iodo-7-(bicyclo[3.2.1]oct-2-yl)-1E-hepten-3-one in 50 ml of absolute ethanol under argon at 0° was added a slurry of 1.6 g (44 mmol) of sodium borohydride in 50 ml of ethanol. The resulting mixture was stirred for 1 hr, and the solvent was removed in vacuo. The residue was taken up in 100 ml of water and extracted with three 100 ml portions of ether. The combined extracts were dried (MgSO$_4$) and evaporated in vacuo to yield 4.0 g (100%) of 1-iodo-7-(bicyclo[3.2.1]-oct-2-yl)-1E-hepten-3RS-ol.

Analysis - IR: $\lambda_{max}^{CHCl_3}$ 10.65μ, 3.43μ, 2.91μ and 2.79μ

NMR(CDCl$_3$): δ4.1, broad, 1H δ6.15 to 6.75, complex, 2H.

F. Preparation of 1-iodo-3RS-(1-ethoxyethoxy)-7-(bicyclo[3.2.1]oct-2-yl)-1E-heptene.

To a solution of 4.0 g (11 mmol) of 1-iodo-7-(bicyclo[3.2.1]oct2-yl)-1E-hepten-3-ol in 15 ml of ethylvinyl ether was added two drops of phosphorus oxychloride. After standing for 18 hr at room temperature the resulting solution was washed with saturated aqueous sodium bicarbonate. The wash solutions was back extracted twice with ether. The combined ether extracts were washed once with saturated aqueous sodium chloride, dried (MgSO$_4$) and evaporated to yield a yellow oil. This yellow oil was chromatographed on silica gel (benezene elution) to yield 1.6 g of 1-iodo-3RS-(1-ethoxyethoxy)-7-(bicyclo[3.2.1]oct-2-yl)-1E-heptene and 1.0 g of the unprotected starting material which was recycled. The spectrum of pure product was:

Analysis - NMR(CDCl$_3$): δ3.24 to 3.73, multiplet, 2H δ3.97, broad, 1H δ4.67, quartet, J=5.3Hz, 1H δ6.08 to 6.65, multiplet, 2H.

EXAMPLE 10

This example illustrates a typical preparaton of 1-iodo-3RS-(1-ethoxyethoxy)-7-(bicyclo[4.4.0]dec-2yl)-1E-heptene.

A. Preparation of 5-(bicyclo[4.4.0]dec-2-ylidene)-pentanoic acid.

Repeating in a similar manner the procedure of Example 9 above but replacing bicyclo[3.2.1]octan-2-one with bicyclo[4.4.0]decan-2-one (1-decalone, Aldrich No. 15,506-3) yields the intermediate 5-(bicyclo[4.4.0]dec-2-ylidene)pentanoic acid.

Analysis - NMR(CDCl$_3$): δ5.0, triplet, J=6.5Hz, 1H δ10.4, broad singlet, 1H

B. Preparation of 5-(bicyclo[4.4.0]dec-2-yl)pentanoic acid.

Repeating in a similar manner the procedure of Example 9B above but replacing 5-(bicyclo[3.2.1]oct-2-ylidene)-pentanoic acid with 5-(bicyclo[4.4.0]oct-2-ylidene)-pentanoic acid yields the intermediate 5-(bicyclo[4.4.0]dec-2-yl)pentanoic acid.

Analysis - NMR(CDCl$_3$): δ10.0, broad singlet, 1H

C. Preparation of 1-chloro-7-(bicyclo[4.4.0]dec-2-yl-1E-hepten-3-one.

Repeating in a similar manner the procedure of Example 9C above, but replacing 5-(bicyclo[3.2.1]oct-2-yl)pentanoic acid with 5-(bicyclo[4.4.0]dec-2-yl)pentanoic acid yields the intermediate 1-chloro-7-(bicyclo[4.4.0]dec-2-yl)-1E-hepten-3-one.

Analysis - NMR(CDCl$_3$): δ2.5, broad triplet, J=6.5Hz, 2H δ6.4, doublet, J=13Hz, 1H δ7.3, doublet, J=13Hz, 1H

D. Preparation of 1-iodo-7-(bicyclo[4.4.0]dec-2-yl)-1E-hepten-3-one.

Repeating in a similar manner the procedure of Example 9D above, but replacing 1-chloro-7-(bicyclo[3.2.1]oct-2-yl)-1E-hepten-3-one with 1-chloro-7-(bicyclo[4.4.0]dec-2-yl)-1E-hepten-3-one yields the intermediate 1iodo-7-(bicyclo[4.4.0]dec-2-yl)-1E-hepten-3-one.

Analysis - NMR(CDCl$_3$): δ2.5, broad triplet, J=6.5Hz, 2H δ7.1, doublet, J=14Hz, 1H δ7.8, doublet, J=14Hz, 1H

E. Preparation of 1-iodo-7-(bicyclo[4.4.0]dec-2-yl)-1E-hepten-3RS-ol.

Repeating in a similar manner the procedure of Example 9E above, but replacing 1-iodo-7-(bicyclo[3.2.1]oct-2-yl)-1E-hepten-3-one with 1-iodo-7-(bicyclo[4.4.0]dec-2-yl)-1E-heptene-3-one yields the intermediate 1-iodo-7-(bicyclo[4.4.0]dec-2-yl)-1E-hepten-3RS-ol.

Analysis - NMR(CDCl$_3$): δ4.17, multiplet, 1H δ6.0 to 7.0, multiplet, 2H

F. Preparation of 1-iodo-3RS-(-ethoxyethoxy)-7-(bicyclo[4.4.0]dec-2-yl)-1E-heptene.

Repeating in a similar manner the procedure of Example 9F above, but replacing 1-iodo-7-(bicyclo[3.2.1]oct-2-yl)-1E-hepten-3RS-ol with 1-iodo-7-(bicyclo[4.4.0]dec-2-yl)-1E-hepten-3RS-ol yields the intermediate 1iodo-3RS-(1-ethoxyethoxy)-7-(bicyclo[4.4.0]dec-2-yl)-1E-heptene.

Analysis - NMR(CDCl$_3$): δ3.5 to 4.2, multiplet, 3H δ4.8, multiplet, 1H δ6.0 to 7.0, multiplet, 2H.

EXAMPLE 11

This example illustrates a typical preparation of 1-iodo-3RS-(1-ethoxyethoxy)-3-(bicyclo[3.2.0]hept-3-yl)-1E-propene.

A. Preparation of cis-1,2,-bis-(hydroxymethyl) cyclobutane.

A solution of 50.0 g (0.40 mmol) of cis-1,2-cyclobutane dicarboxylic anhydride (Aldrich No. 14,543-2) in 50 ml of ether and 75 ml of THF was added in small portions to a 0° C slurry of 21.0 g of lithium aluminum hydride in 210 ml of ether in a 500 ml three-necked round bottomed flask equipped with a reflux condenser, mechanical stirring, addition funnel and argon inlet. The reaction mixture was warmed to 50° C and stirred for 1 hr. Ethyl acetate (51.0 ml) was added dropwise, followed by 21.0 ml water, 21.0 ml 15% aqueous sodium hydroxide and 40 ml of water. The reaction mixture was stirred for 18 hr at 25° C, then filtered. The filtrate was eashed with brine and vacuum distilled to afford 21.5 g of cis-1,2-bis-hydroxymethyl)cyclobutane as a clear oil, bp 94°-97° (vacuum pump).

Analysis - IR: $\lambda_{max}^{CHCl_3}$ 2.78μ, 3.0μ(broad), 5.9μ

NMR(CDCl$_3$): δ1.10–2.30, multiplet, 4H, CH$_2$-CH, δ2.65, multiplet, 2H, CH-CH δ3.60, multiplet, 4H, CH$_2$OH δ4.65, broad t, 2H, OH.

B. Preparation of cis-1,2-bis(bromoethyl)cyclobutane.

To 44 g of phosphorus tribromide (−10° C) was added dropwise 10.7 g of distilled cis-1,2-bis(hydroxymethyl)cyclobutane over a 1 hr period. The reaction mixture was warmed to 25° C and stirred for 2 hr, then heated to 80-85° for 18 hr. The reaction mixture was cooled in ice and cold water added. The layers were separated and the aqueous layer was extracted with methylene chloride. The organic extracts were combined, washed with 5% aqueous sodium carbonate and water, then distilled to yield 13.8 g of cis-1,2-bis(-bromomethyl)cyclobutane as a purple oil, bp 86° C (vacuum pump).

Analysis - IR: $\lambda_{max}^{CHCl_3}$ 3.4μ, 7.0μ, 8.1μ (no OH signal observed)

NMR(CDCl$_3$): δ1.3–2.5, multiplet, 4H, CH$_2$-CH$_2$ δ2.8, multiplet, 2H, CH-CH δ3.5, multiplet, 2H, CH$_2$Br.

C. Preparation of 3,3-bis(ethoxycarbonyl)bicyclo[3.2.0]heptane.

In a 250 ml round-bottomed flask equipped with mechanical stirring, reflux condenser, addition funnel and argon inlet was placed 20.2 g of cis-1,2-bis(bromomethyl)cyclobutane, 12.4 ml diethylmalonate, and 72 ml of dry t-butanol. The reaction mixture was refluxed and a solution of 19.9 g of potassium-t-butoxide in 123 ml of t-butanol was added over 6.0 hr. The reaction mixture was refluxed for 15 hr. The reaction mixture was cooled by external application of an ice-water bath and an equal volume of water added. The mixture was extracted with ether. The ether extracts were washed with 3 N hydrochloric acid and 5% aqueous sodium bicarbonate, then dried (MgSO$_4$), filtered and distilled in vacuo to yield 10.3 g of 3,3-bis(ethoxycarbonyl)bicyclo[3.2.0]heptane as a clear oil, bp 100°–105° C (vacuum pump).

Analysis - IR: $\lambda_{max}^{CHCl_3}$ 5.85μ

NMR(CDCl$_3$): δ1.22, pair of t, J=7.0Hz, broad, CH$_2$CH$_3$ δ4.37 quartet, 4H, CH$_2$CH$_3$.

D. Preparation of bicyclo[3.2.0]heptane-3,3-dicarboxylic acid.

A solution of 10.3 g of 3,3-bis(ethoxycarbonyl)bicyclo[3.2.0]heptane in 68 ml of 16% potassium hydroxide in 1:1 methanol-water was refluxed for 16 hr under argon. The solvents were removed in vacuo and the residue dissolved in a minimum amount of water. The solution was acidified with concentrated hydrochloric acid and the precipitated acid isolated by vacuum filtration to yield 6.9 g of bicyclo[3.2.0]heptane-3,3-dicarboxylic acid as a white solid, mp 161°–170°.

Analysis - NMR(DMSO-d$_6$): δ7.65, broad singlet, 2H, CO$_2$H.

E. Preparation of cis-(bicyclo[3.2.0]hept-3-yl)carboxylic acid.

Bicyclo[3.2.0]heptane-3,3-dicarboxylic acid (6.90 g) was heated at 190° under argon for 1 hr to afford 4.75 g of cis-(bicyclo[3.2.0]hept-3-yl)carboxylic acid as a brown oily solid.

Analysis - NMR(CDCl$_3$): δ10.18, broad singlet, 1H, CO$_2$H IR(CHCl$_3$): 2.75–4.4μ(broad), 5.85μ, 6.40μ.

F. Preparation of 1-chloro-3-(bicyclo[3.2.0]hept-3-yl)-1E-propen-3-one.

Repeating in a similar manner the procedure of Example 9C above, but replacing 5-(bicyclo[3.2.1]oct-2-yl)pentanoic acid with bicyclo[3.2.0]heptane-3-carboxylic acid yields the intermediate 1-chloro-3-(bicyclo[3.2.0]-hept-3-yl)-1E-propen-3-one.

Analysis - NMR(CDCl$_3$): δ6.66, doublet, J=14Hz, 1H δ7.36, doublet, J=14Hz, 1H.

G. Preparation of 1-iodo-3-(bicyclo[3.2.0]hept-3-yl)-1E-propen-3-one.

Repeating in a similar manner the procedure of 9D above, but replacing 1-chloro-7-(bicyclo[3.2.1]oct-2-yl)-1E-hepten-3-one with 1-chloro-3-(bicyclo[3.2.0]hept-3-yl)-1E-propen-3-one to yield the intermediate 1-iodo-3-(bicyclo[3.2.0]hept-3-yl)-1E-propen-3-one.

Analysis - NMR(CDCl$_3$): δ7.27, doublet, J=15Hz, 1H δ7.99, doublet, J=15Hz, 1H

H. Preparation of 1-iodo-3-(bicyclo[3.2.0]hept-3-yl)-1E-propen-3RS-ol.

Repeating in a similar manner the procedure of 9E above, but replacing 1-iodo-7-(bicyclo[3.2.1]oct-2-yl)-1E-hepten-3-one with 1-iodo-3-(bicyclo[3.2.0]hept-3-yl)-1E-propen-3-one yields the intermediate 1-iodo-3-(bicyclo[3.2.0]-hept-3-yl)-1E-propen-3RS-ol.

Analysis - NMR(CDCl$_3$): δ4.2, multiplet, 1H δ6.26, doublet, J=15Hz,1H δ6.62, doublet of doublets, J=15 and 6Hz, 1H.

I. Preparation of 1-iodo-3RS-(1-ethoxyethoxy)-3-(bicyclo[3.2.0]hept-3-yl)-1E-propane.

Repeating in a similar manner the procedure of 9F above, but replacing 1-iodo-7-(bicyclo[3.2.1]oct-3-yl)-1E-hepten-3RS-ol with 1-iodo-3-(bicyclo[3.2.0]hept-3-yl)-1E-propen-3RS-ol yields the intermediate 1-iodo-3RS-(1-ethoxyethoxy)-3-(bicyclo[3.2.0]hept-3-yl)-1E-propene.

Analysis - NMR(CDCl$_3$): δ3.5 to 4.2, multiplet, 3H δ4.8, multiplet, 1H δ6.0 to 7.0, multiplet, 2H.

EXAMPLE 12

This example illustrates a typical preparation of 1-iodo-3RS-(1-ethoxyethoxy)-4-(bicyclo[2.2.1]hept-2-yl)-1E-butene.

A. Preparation of 1-chloro-4-(bicyclo[2.2.1]hept-2-yl)-1E-propen-3-one.

Repeating in a similar manner the procedure of Example 9C above replacing 5-(bicyclo[3.2.1]oct-2-yl)pentanoic acid with (bicyclo[3.2.1]hept-2-yl)acetic acid (Aldrich No. 12,7264) yields the intermediate 1-chloro-4-(bicyclo[2.2.1]hept-2-yl-1E-propen-3-one.

Analysis - NMR(CDCl$_3$): δ6.2, doublet, J=13Hz, 1H δ6.95, doublet, J=13Hz, 1H.

B. Preparation of 1-iodo-4-(bicyclo[2.2.1]hept-2-yl)-1E-propen-3-one.

Repeating in a similar manner the procedure of Example 9D above but replacing 1-chloro-7-(bicyclo[3.2.1]oct-2-yl)-hept-2-yl)-1E-propen-3-one with 1-chloro-4-(bicyclo[2.2.1]-hept-2-yl)-1E-propen-3-one yields the intermediate 1-iodo-4-(bicyclo[2.2.1]hept-2-yl)-1E-propen-3-one.

Analysis - NMR(CDCl$_3$): δ7.20, doublet, J=15Hz, 1H δ7.85, doublet, J=15Hz, 1H.

C. Preparation of 1-iodo-4-(bicyclo[2.2.1]hept-2-yl)-1E-propen-3RS-ol.

Repeating in a similar manner the procedure of Example 9E above, but replacing 1-iodo-7-(bicyclo[3.2.1]oct-2-yl)-1E-hepten-3-one with 1-iodo-4-(bicyclo[2.2.1]hept-2-yl)-1E-propen-3-one yields the intermediate 1-iodo-4-(bicyclo[2.2.1]hept-2-yl)-1E-propen-3RS-ol.

Analysis - NMR(CDCl$_3$): δ5.04, multiplet, 1H δ6.1 to 6.8, multiplet, 2H.

D. Preparation of 1-iodo-3RS-(1-ethoxyethoxy)-4-(bicyclo[2.2.1]hept-2-yl)-1E-butene.

Repeating in a similar manner the procedure of Example 9F above, but replacing 1-iodo-7-(bicyclo[3.2.-

1]oct-2-yl)-1E-hepten-3RS-ol with 1-iodo-4-(bicyclo[2.2.1]hept-2-yl)-1E-propen-3RS-ol yields the intermediate 1-iodo-3RS-(1-ethoxyethoxy)-4-(bicyclo[2.2.1]hept-2-yl)-1E-butene.

Analysis - NMR(CDCl$_3$): δ3.5, multiplet, 3H δ4.7, multiplet, 1H δ6.1 to 6.6, multiplet, 2H.

EXAMPLE 13

This example illustrates a typical preparation of methyl 7-(6-oxocyclohex-1-enyl)hept-5Z-enoate.

A. Preparation of 7-oxabicyclo[4.3.0]non-2-en-8-one.

This compound was prepared by following the procedures of E. J. Corey and T. Ravindranathan, *Tetrahedron Letters*, 4753 (1971).

A solution of 13.8 g of the above compound in 100 ml of dry methylene chloride (passed through Woelm activity grade I alumina prior to use) was stirred at −78° under argon as 19.0 ml (107 mmol) of diisobutylaluminum hydride was added dropwise over 0.5 hr. After 3 hr at −78° the reaction mixture was quenched at −78° by the slow addition of several ml of 10% aqueous hydrochloric acid. The resultant mixture was diluted with 200 ml of methylene chloride. The mixture was then stirred in an ice-water bath as 100 ml of 10% hydrochloric acid was added dropwise. The layers which formed were separated and the aqueous phase was extracted twice more with methylene chloride. The combined methylene chloride extracts were washed with brine and then with saturated aqueous sodium bicarbonate. The washed extract was dried (Na$_2$SO$_4$) and evaporated in vacuo to yield 12.3 g of 7-oxabicyclo[4.3.0]non-2-en-8-ol.

Analysis - IR: $\lambda_{max}^{CHCl_3}$ 14.3μ, 13.7μ, 10.87μ, 9.90μ, 9.61μ, 9.27μ, 6.90μ, 3.40μ and 2.78 to 3.13(broad)

NMR(CDCl$_3$): δ1.0 to 3.0, multiplet, 7H δ4.0 to 4.8, multiplet, 2H δ5.2 to 6.0, multiplet, 3H.

B. Preparation of 7-(6-hydroxycyclohex-2-enyl)hept-5Z-enoic acid.

A 12.5 g (296 mmol) portion of sodium hydride (57% oil dispersion) was heated with 95 ml of dry dimethylsulfoxide (DMSO) under argon at 65°–75° for ca. 2.5 hr until hydrogen evolution had ceased. The mixture was stirred with ice-water cooling as 48.3 g (109 mmol) of 4-carboxybutyltriphenylphosphonium bromide (Aldrich) was added as a solid. The resultant deep red mixture was stirred at 0° for several minutes, then at room temperature until most of the salts had dissolved (1 hr.). A solution of 12.2 g (87.1 mmol) of 7-oxabicyclo[4.3.0]-non-2-en-8-ol in 10 ml of dry DMSO was added dropwise over 2 hr to the vigorously stirred ylide solution. The resultant dark mixture was stirred for 20 hr at room temperature. Water (200 ml) was added then and the resultant mixture was extracted three times with ethyl acetate and these extracts were discarded. The remaining aqueous phase was acidified with concentrated hydrochloric acid and then extracted four times with ethyl acetate. The combined extracts were dried (MgSO$_4$) and evaporated in vacuo. The resultant residue was evaporated at 0.1 mm as the pot was warmed to 50° and the receiver flask was cooled in an acetone-dry bath. The yield of crude orange oil was 32.5 g (theoretical yield 19.5 g) and contained in addition to the desired product, considerable aromatic byproduct as evidenced from an nmr spectrum of this oil. This oil was extracted several times with warm ether-pentane (1:1). The combined extracts were dried (MgSO$_4$) and evaporated in vacuo to give 11.9 g of 7-(6-hydroxycyclohex-2-enyl)-hept-5Z-enoic acid. A portion of this product was purified by column chromatography on silicic acid-Celite (85:15) using benzene to ethyl acetate gradient elution to obtain pure 7-(6-hydroxycyclohex-2-enyl)hept-5Z-enoic acid.

Analysis - IR: $\lambda_{max}^{CHCl_3}$ 9.35μ, 8.08μ, 7.10μ, 6.95μ, 5.85μ, 3.40μ and 2.78μ to 4.17μ(broad)

NMR(CDCl$_3$): δ1.1 to 2.8, multiplet, 13H δ2.1, multiplet, 1H δ5.2 to 6.3, multiplet, 6H Mass Spectrum (70 eV): m/e 224, 220, 206, 147, 133, 127, 119, 105, 97, 91, 80, 79(base), 67 and 55.

C. Preparation of 7-(6-oxocyclohex-2-enyl)hept-5Z-enoic acid.

A solution of 15.8 g of 7-(6-hydroxycyclohex-2-enyl)-hept-5Z-enoic acid (as obtained by ether-pentane extraction as described above) in 300 ml of acetone was stirred with ice-bath cooling as 30 ml of standard Jones reagent was added dropwise. The resultant mixture was stirred for 10 min at 0° and then quenched by the addition of several ml of isopropyl alcohol. After stirring for another 10 min at 0° the solvents were removed by evaporation in vacuo. The residue was dissolved in water and extracted several times with ether. The combined ether extracts were washed with brine, dried (MgSO$_4$) and evaporated in vacuo to yield 13.0 g of crude 7-(6-oxocyclohex-2-enyl)hept-5Z-enoic acid as a yellow oil.

Analysis - IR: $\lambda_{max}^{film}$ 952μ, 8.07μ, 7.09μ, 6.95μ, 5.85μ, 3.40μ, 3.37μ and 2.78μ to 4.17μ(broad)

NMR(CDCl$_3$): δ1.3 to 3.2, multiplet, 13H δ5.2 to 6.2, multiplet, 4H δ8.5, broad singlet, 1H.

D. Preparation of Methyl 7-(6-oxyocyclohex-1-enyl)-hept-5Z-enoate.

A solution of 13.0 g of crude 7-(6-oxocyclohex-2-enyl)hept-5Z-enoic acid in 200 ml of dry methanol was stirred under argon as 2 ml of acetyl chloride was added. The resultant yellow solution was left to stand for 2.6 days (on another occasion 16 hr was found to be sufficient). Solvent was removed by evaporation in vacuo and the residue was dissolved in ether and washed with saturated aqueous sodium bicarbonate. The wash solution was back extracted with ether. The combined ether extracts were dried (MgSO$_4$) and evaporated in vacuo to yield 11.6 g of crude methyl 7-(6-oxocyclohex-1-enyl)hept-5Z-enoate as a yellow oil. This product was purified by chromatography on silicic acid-Celite (85:15) using benzene to ethyl acetate gradient elution to give 0.78 g of ca. 80% pure material and 8.41 g of pure material.

Analysis - IR: $\lambda_{max}^{film}$ 9.17μ, 8.55μ, 8.33μ, 8.00μ, 7.30μ, 7.04μ, 5.95μ, 5.74μ and 3.39μ

NMR(CDCl$_3$): δ1.3 to 2.5, multiplet, 12H δ2.9, multiplet, 2H δ3.67, singlet, 3H δ5.45, multiplet, 2H δ6.7, multiplet, 1H.

EXAMPLE 14

A. Evaluation of Inhibition of Human Platelet Aggregation by Analogues of Prostaglandins Structure III.

The ability of test compounds to inhibit platelet aggreagation was determined by a modification of the turbidometric technique of Born (Nature, 194: 927 [1962]). Blood was collected from human volunteer who had not ingested aspirin or aspirin-containing